United States Patent [19]
Atsumi

[11] Patent Number: 5,421,807
[45] Date of Patent: Jun. 6, 1995

[54] CIRCULATORY ASSIST SYSTEM

[75] Inventor: Takafumi Atsumi, Anjo, Japan

[73] Assignees: Aisin Seiki Kabushiki Kaisha, Kariya; Kabushiki Kaisha Shinsangyokaihatsu, Tokyo, both of Japan

[21] Appl. No.: 197,865

[22] Filed: Feb. 17, 1994

[30] Foreign Application Priority Data

Feb. 19, 1993 [JP] Japan ................... 5-030512

[51] Int. Cl.6 ............................................ A61B 19/00
[52] U.S. Cl. ............................................... 600/16
[58] Field of Search ................... 600/16, 17, 18; 128/672, 673

[56] References Cited

U.S. PATENT DOCUMENTS 5,045,051 9/1991 Milder et al. ...................... 600/16
5,169,379 12/1992 Freed et al. ........................ 600/18

FOREIGN PATENT DOCUMENTS 3-63068 3/1991 Japan .

*Primary Examiner*—George Manuel
*Attorney, Agent, or Firm*—Burns, Doane, Swecker & Mathis

[57] ABSTRACT

A circulatory assist system includes a blood pump, a tube connected at one end portion thereof to the blood pump and having an inner space, a driving device having an outlet connected to the other end portion of the tube for applying a gas to the blood pump in such a manner that the blood pump is inflated and deflated alternately, and a drain device positioned near the outlet of the driving device and having a reservoir space into which water drops fall from the inner space of the tube.

8 Claims, 3 Drawing Sheets

5,421,807

CIRCULATORY ASSIST SYSTEM

BACKGROUND OF THE INVENTION

The present invention relates to a circulatory assist system.

In general, in a conventional circulatory assist system a blood pump is expected to be inflated and deflated alternately by introducing and discharging a shuttle gas, respectively, from a driving device via a tube. During deflation of the blood pump, an outer surface of the blood pump is in contact with the blood of a patient and the pressure within the blood pump is less than that of the blood per so that the thin membrane or film of the raw material of the blood pump allows vapour in the blood to enter into the shuttle gas. The resultant vapour enters the tube and is formed into water drops which are apt to disturb the flow of the shuttle gas. For avoiding such a problem, a drain device is provided in the circulatory assist system in order that the water drops fall into the drain device.

in Japanese Patent Laid-open Print No. Hei 3, (1991)-63068 published on Mar. 19, 1991 without examination, the water drops fall by gravity into a drain device. An outlet of the driving device through which the shuttle gas passes, the tube except for a portion at which the blood pump is connected and the drain device should be extended along a vertical line. Thus, the position of the drain device is fixed in effect. This means that if the drain device is located at an unexpected position, the water drops rail to fall into the drain device and remain in the tube which leads to a disturbance of the flow of the shuttle gas.

SUMMARY OF THE INVENTION

It is, therefore, an object of the present invention is to provide a circulatory assist system without the foregoing drawbacks.

Another object of the present invention is to provide a circulatory assist system in which water drops are condensed by heat.

In order to attain the foregoing objects, a circulatory assist system comprises a blood pump; a tube connected at one end portion thereof to the blood pump and having an inner space; a driving device having an outlet connected to the other end portion of the tube for applying a gas to the blood pump in such a manner that the blood pump is inflated and deflated alternately; and a drain device positioned near the outlet of the driving device and having a reservoir space into which water drops fall from the inner space of the tube.

BRIEF DESCRIPTION OF THE DRAWINGS

The above and other objects, features and advantages of the present invention will be more apparent and more readily appreciated from the following detailed description of preferred exemplarily embodiments of the present invention, taken in connection with the accompanying drawings, in which.

DESCRIPTION OF A PREFERRED EMBODIMENT

A preferred embodiment of the present invention will be described hereinunder in detail with reference to the accompanying drawings.

Figure 1:
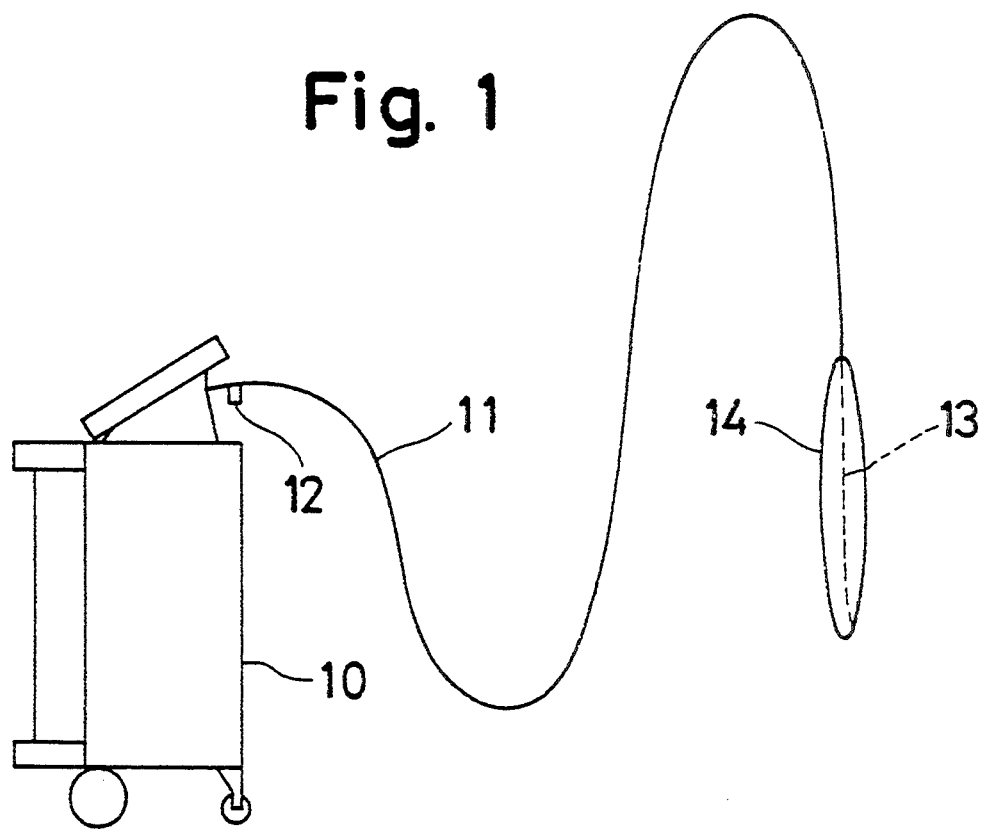
FIG. 1 shows an outline of a circulatory assist system in accordance with the present invention.

Referring first to FIG. 1, a blood pump driving device 10 is connected to a blood pump 13 of an artificial pump 14 via a tube 11 provided with a drain device 12.

Figure 2:
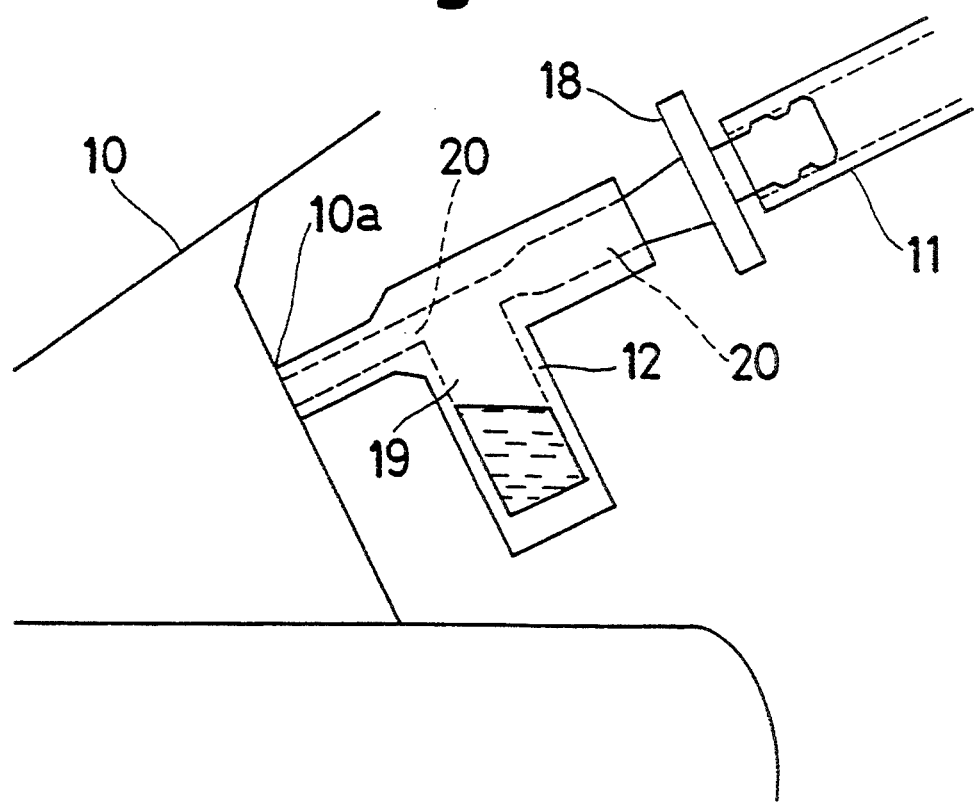
FIG. 2 shows a principal portion of a circulatory assist system shown in FIG. 1.
Figure 3:
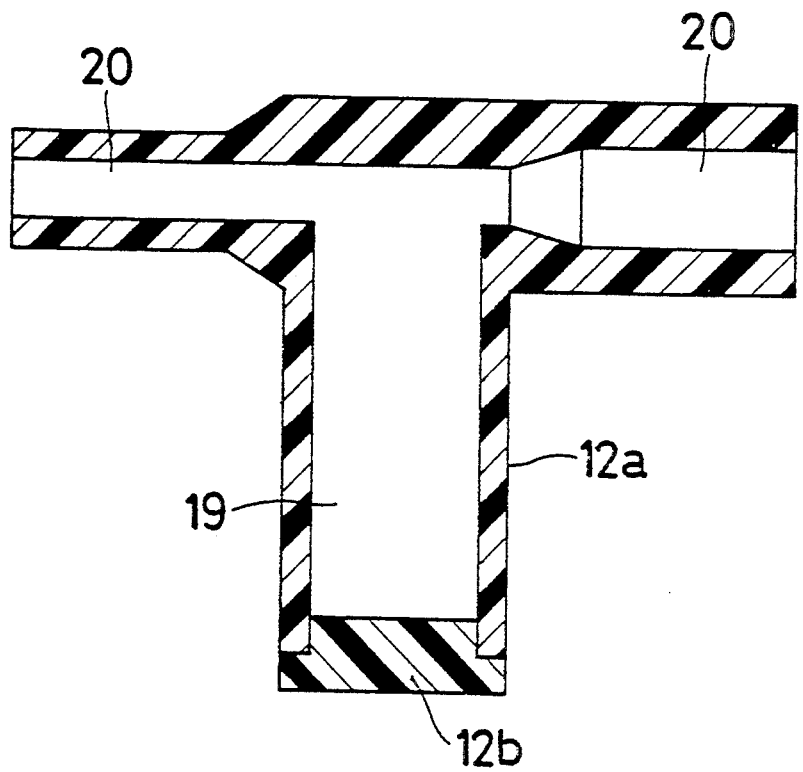
FIG. 3 is a cross-sectional view of a drain device.

As shown in FIGS. 2 and 3, the drain device 12 includes a body 12a in which a pair of passages 20 and a reservoir space or portion 19 are formed. A plug 12b is used for closing an open bottom of the reservoir portion 19. The plug 12b is detachably secured or adhered to the body 12a. One of the passages 20 is detachably connected to an outlet port 10a of the blood pump driving device 10 and the other end is connected detachably to a plug 18 which is detachably connected to the tube 11. The reservoir portion 19 has a smooth inner surface and is in the form of a cylindrical configuration, in order that water can he drained therealong without stagnation when the drain device 12 is tilted or reversed.

Figure 4:
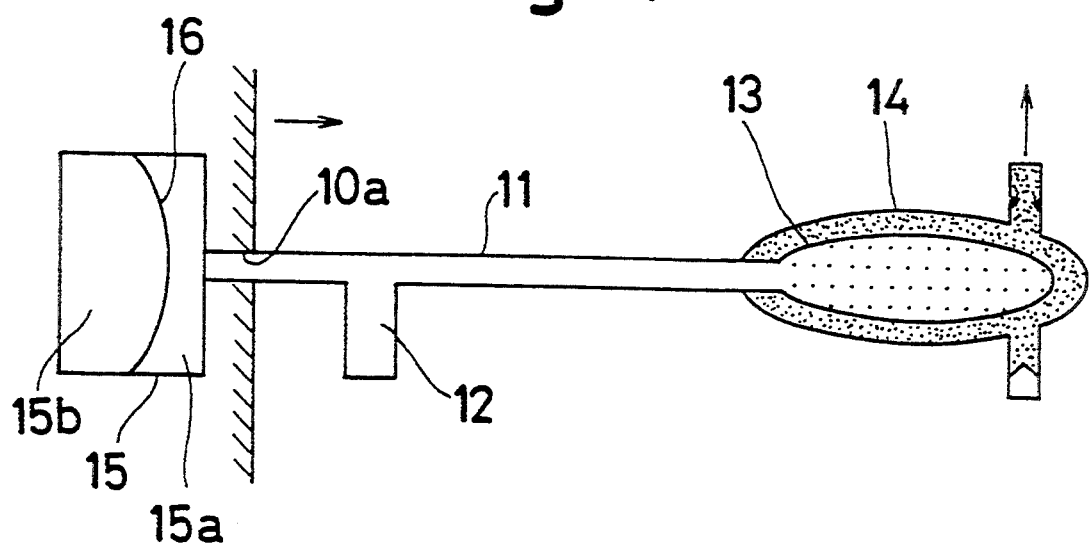
FIG. 4 and FIG. 5 show an operation of a circulatory assist system shown in FIG. 1: and FIG. is a cross-sectional view of another drain device.
Figure 5:
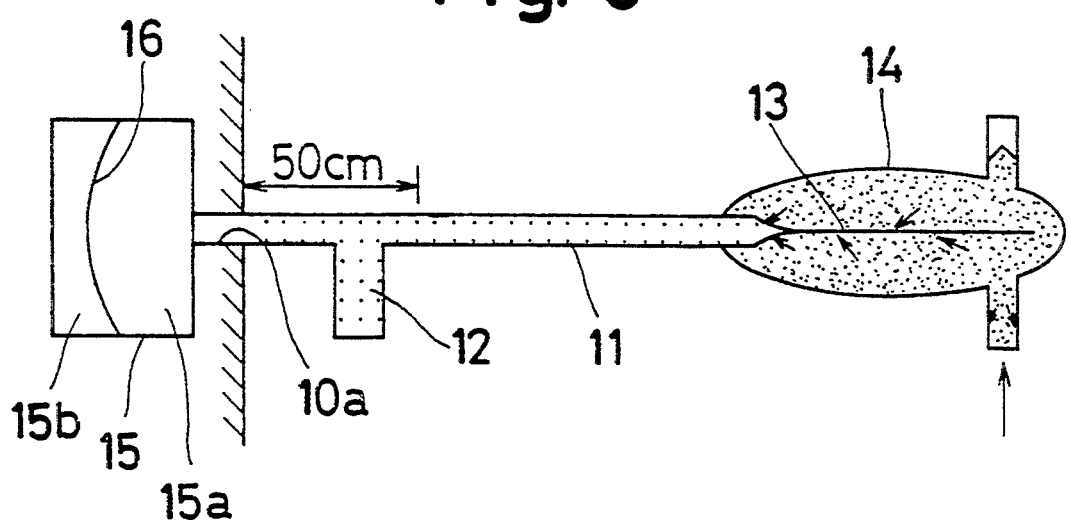

As can he seen From FIG. 4, within the blood pump driving device 10, there is provided an isolator 15 having an inner space. The inner space is divided by a membrane 16 into a right chamber 15a and a left chamber 15b. The right chamber 15a, which can be regarded as an outlet side of the blood pump driving device 10, is connected to the tube 11. After completing assembly of the right chamber 15a of the isolator 15, the tube 11, the drain device 12 and the blood pump 13 of the artificial pump 14, a shuttle gas which is harmless for persons such, as a helium gas is filled within a whole continuous space ranging from the the right chamber 15a of the isolator 15 to the the blood pump 13 of the artificial pump 14. Adjusting a pressure within the left chamber 15b of the isolator 15 will displace the membrane 16 which results in driving the blood pump 13. That is to say, if the membrane 16 is displaced in the rightward direction (leftward direction), the pressure in the right chamber 15a is increased (decreased) which leads to an inflation (a deflation) of the blood pump 13. Thus, the blood is expelled (sucked).

During deflation of the blood pump 13, an outer surface of the blood pump 13 is in contact with the blood and the pressure within the blood pump 13 is less than that of the blood per se. Thus, the thin membrane or film of the raw material of the blood pump 13 allows the entrance of vapour in the blood into the shuttle gas. The resultant vapour will enter the tube 11 during the reciprocal movement of the membrane 16 for increasing and decreasing the pressure in the chamber 15a alternately. In light of the fact that the isolator 15 is in association with a compressor and other elements in the blood pump driving device 10 which are expected to be electrically operated or driven, heat is generated in the vicinity of the blood pump driving device 10. The vapours which enter the tube 11 will be condensed into water drops due to the pressure increase and a temperature difference between the tube 11 and the blood pump driving device 10. Given the fact that the heat capacity of the drain device 12 is relatively high, water drops tend to be generated or formed at the drain device 12. Thus, water drops are concentrated at the drain device 12 and fall into the reservoir portion 19. In addition, other water drops on an inner surface of the tube 11 are expected to be moved therealong according to the alternately of increasing and decreasing pressure, and during the resultant movement the water drops fall into the reservoir portion 19 in the long run. Since the reservoir portion 19 is offset from the movement path of the shuttle gas which results in little shuttle gas flowing in the reservoir portion 19, most of the water is at rest and fails to re-enter the tube 11. Thus, the cross-section of the tube 11 is prevented from being reduced by water drops.

When the reservoir portion 19 is filled with water, removing the drain device 12 from the outlet port 10a of the blood pump driving device 10 and reversing the same will establish a drainage easily. The reason is that the inner surface of the reservoir portion 19 is of smooth a configuration, which ensures that water is drained without stagnation. It is to be noted that at this time the reservoir portion 19 may be removed from the plug 18.

Since the drain device 12 is positioned near the outlet port of the blood pump driving device 10, the temperature difference therebetween becomes large, which results in water drops being likely to be formed at the drain device 12. In particular, at a position within 50 cm outside the the outlet port of the blood pump driving device 10, this phenomena can be remarkably found. Thus, locating the drain device 12 at this position is desirable.

Depending on the volume of the blood pump 13, the volume of each of the tube 11 and the drain device 12 can be adjusted.

Figure 6:
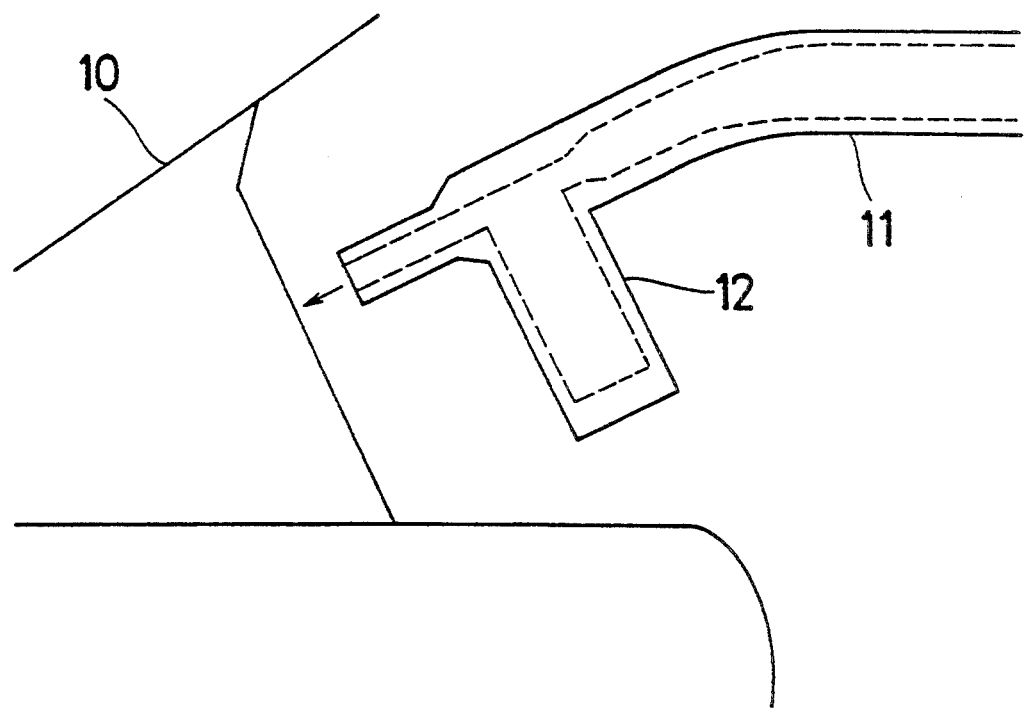

As can be seen from FIG. 2, the drain device 12 is simple in construction and is detachable to each of the blood pump driving device 10 and the tube 11. Instead of this, as shown in FIG. 6, the the drain device 12 can be formed integrally with the tube 11.

Instead of the the blood pump 13 of an artificial pump 14, an intra-aortic balloon pump or other device is available.

The invention has thus been shown and described with reference to a specific embodiment, however, it should be noted that the invention is in no way limited to the details of the illustrated structures but changes and modifications may be made without departing from the scope of the appended claims.

What is claimed is:

1. A circulatory assist system comprising:
   a blood pump;
   a tube having oppositely located first and second end portions and an inner space, said first end portion of the tube being connected to the bloom pump;
   a driving device for applying a gas to the blood pump in such a manner that the blood pump is alternately inflated and deflated said driving device having an outlet; and
   a drain device positioned near the outlet of the driving device between the second end of the tube and the outlet of the driving device, said drain device having a reservoir space into which water drops fall from the inner space of the tube.

2. A circulatory assist system in accordance with claim 1, wherein the reservoir space of the drain device is offset from movement path of the gas between the driving device and the blood pump.

3. A circulatory assist system in accordance with claim 1, wherein the drain device is detachably connected to the outlet of the driving device and to the second end of the tube.

4. A circulatory assist system in accordance with claim 1, wherein the drain device is detachably connected to the driving device and is formed integrally with the tube.

5. A circulatory assist system in accordance with claim 1, wherein the reservoir space of the drain device possesses a smooth inner surface.

6. A circulatory assist system in accordance with claim 5, wherein the inner surface of the reservoir space possesses a cylindrical configuration.

7. A circulatory assist system in accordance with claim 1, wherein said drain device is directly connected to the outlet of the driving device.

8. A circulatory assist system in accordance with claim 1, wherein the shuttle gas moves through the drain device along a straight movement path, the reservoir portion of the drain device being located below said straight movement path.

* * * * *